United States Patent [19]
Steventon

[11] Patent Number: 6,129,906
[45] Date of Patent: *Oct. 10, 2000

[54] SILICONE CONTAINING POWDERS

[75] Inventor: Anthony James Steventon, Farnham, United Kingdom

[73] Assignee: The Procter & Gamble Company, Cincinnati, Ohio

[*] Notice: This patent is subject to a terminal disclaimer.

[21] Appl. No.: 09/068,596

[22] PCT Filed: Oct. 25, 1996

[86] PCT No.: PCT/US96/17124

§ 371 Date: Oct. 2, 1998

§ 102(e) Date: Oct. 2, 1998

[87] PCT Pub. No.: WO97/17939

PCT Pub. Date: May 22, 1997

[30] Foreign Application Priority Data

Nov. 11, 1995 [GB] United Kingdom .................. 9523136

[51] Int. Cl.[7] .............. A61K 7/20; A61K 9/14; A61K 9/20; A61K 9/46
[52] U.S. Cl. ............... 424/49; 424/44; 424/464; 424/466; 424/489
[58] Field of Search ............... 424/53, 408, 409, 424/417, 464, 466, 489, 44

[56] References Cited

U.S. PATENT DOCUMENTS

| | | | |
|---|---|---|---|
| Re. 35,893 | 9/1998 | Valentine et al. | 424/489 |
| 4,421,666 | 12/1983 | Hempel et al. | 252/140 |
| 5,073,365 | 12/1991 | Katz et al. | 424/489 |
| 5,073,384 | 12/1991 | Valentine et al. | 424/474 |
| 5,089,256 | 2/1992 | Scheller et al. | 424/63 |
| 5,126,151 | 6/1992 | Boder et al. | 426/99 |
| 5,149,521 | 9/1992 | Hirose et al. | 424/58 |
| 5,176,903 | 1/1993 | Goldberg et al. | 424/61 |
| 5,194,262 | 3/1993 | Goldberg et al. | 424/401 |
| 5,206,010 | 4/1993 | Inoue et al. | 424/49 |
| 5,271,934 | 12/1993 | Goldberg et al. | 424/401 |
| 5,275,822 | 1/1994 | Valentine et al. | 424/489 |
| 5,370,881 | 12/1994 | Fuisz | 426/5 |
| 5,490,982 | 2/1996 | Siciliano | 424/401 |
| 5,545,342 | 8/1996 | Beagle et al. | 510/299 |
| 5,560,917 | 10/1996 | Cohen et al. | 424/401 |
| 5,665,368 | 9/1997 | Lentini et al. | 424/401 |
| 5,753,607 | 5/1998 | Burke et al. | 510/42 |
| 5,759,523 | 6/1998 | Hughes et al. | 424/53 |
| 5,770,556 | 6/1998 | Farrell et al. | 510/447 |
| 5,827,505 | 10/1998 | Hughes et al. | 424/49 |
| 5,856,282 | 1/1999 | Hughes et al. | 510/117 |
| 5,871,720 | 2/1999 | Gutierrez et al. | 424/65 |

FOREIGN PATENT DOCUMENTS

| | | | |
|---|---|---|---|
| 0 550 067 B1 | 7/1993 | European Pat. Off. | A23L 1/22 |
| 1-081856 | 3/1989 | Japan | A61K 7/16 |

*Primary Examiner*—Shep K. Rose
*Attorney, Agent, or Firm*—Betty J. Zea

[57] ABSTRACT

A spray-dried, granular powder comprising: (i) from about 50% to about 99% of a water-soluble carrier, (ii) from about 1% to about 50% of a hydrophobic silicone oil dispersed within the carrier, wherein the spray-dried powder has a volume average particle size in the range from about 20 $\mu$m to about 500 $\mu$m, the powder being prepared by spray-drying an aqueous dispersion of the silicone oil and the water-soluble carrier, characterized in that the silicone oil is present in the dispersion in the form of discrete droplets having a volume average droplet size in the range from about 0.5 $\mu$m to about 20 $\mu$m and that the ratio of the average spray-dried particle size to the average droplet size is at least about 2.5:1. The powder is dry, free-flowing and processable into a punched tablet or other compressed forms, yet efficiently delivers the silicone oil on subsequent dissolution in water.

17 Claims, No Drawings

SILICONE CONTAINING POWDERS

TECHNICAL FIELD

The present invention relates to granular powders comprising hydrophobic silicone oils. In particular, the invention relates to powders comprising hydrophobic silicone oils which can be incorporated into dental preparations in solid form, such as denture cleanser tablets, toothpowders and the like, to deliver enhanced antiplaque activity together with excellent cleansing performance, physical characteristics, and in-use performance characteristics.

BACKGROUND

Plaque is initiated when bacteria adhered to pellicle form a proteinaceous film on the surface of teeth. The adherent bacteria metabolise dietary constituents and reproduce and aggregate to form the tenacious deposit known as plaque. Plaque generally consists of bacteria, bacterial end products such as polysaccharides, inorganic salts and salivary proteins. Plaque bacteria ferment dietary carbohydrates to organic acids which demineralize enamel resulting in tooth decay.

Calculus is essentially plaque that has been mineralised with calcium phosphate salts. As calculus matures and hardens, it tends to stain noticeably due to adsorption of dietary chromagens. In addition to their unattractive appearance, calculus deposits at the gum line are a contributing source of gingivitis and periodontal disease. Besides the hygienic and health problems resulting from plaque, research has shown that the primary source of bad breath is the retention and subsequent degradation of dead cellular material sloughed off continuously by the normal, healthy mouth. Modern dental hygiene and denture preparations typically contain antiplaque and/or antitartar agents, as well as antimicrobial agents and flavorants. Antimicrobial action could affect plaque formation by either reducing the number of bacteria in the mouth/dentures or by killing those bacteria trapped in the film to prevent further growth and metabolism. Flavorants may alleviate the problem of bad breath via a deodorizing action. Some antimicrobial agents, e.g. menthol, may also serve as breath deodorizers. However, the efficacy of antimicrobial agents depends largely on their intraoral/denture retention, particularly their retention on the surface of the teeth or dentures where plaque is formed.

A typical disadvantage of known dental preparations is that only a relatively short time during which the teeth are being cleaned or the mouth is being rinsed is available for antimicrobial agents in the preparations to take effect. The problem is compounded by the fact that dentifrice preparations are used infrequently: most are used once or, perhaps, twice daily. Consequently, the long time period between brushings for a majority of the population provides optimum plaque forming conditions.

There has been a need, therefore, for developing an oral formulation which has a prolonged, residual antimicrobial and/or flavor impact effect.

It is known to include silicones in dentifrice compositions, allegedly to coat the teeth and prevent cavities and staining. For instance, GB-A-689,679 discloses a mouthwash containing an organopolysiloxane for preventing adhesion of, or for removing tars, stains, tartar and food particles from the teeth. The mouthwash can include antiseptic compounds, such as thymol, and flavoring and perfuming agents.

U.S. Pat. No. 2,806,814 discloses dental preparations including, in combination, a higher aliphatic acyl amide of an amino carboxylic acid compound as an active and a silicone compound. The patent notes that silicone compounds have been proposed for prevention of adhesion or to facilitate the removal of tars, stains, tartar and the like from teeth. The silicone compound is said to act as a synergist in improving the antibacterial and acid inhibiting activity of the active ingredient. Dimethyl polysiloxanes are said to be particularly effective. Flavoring oils and/or menthol may be included.

U.S. Pat. No. 3,624,120 discloses quaternary ammonium salts of cyclic siloxane polymers for use as cationic surfactants, bactericides and as anticariogenic agents.

However, most silicones, useful for the purpose of plaque prevention, are liquid at room temperature, and can present problems of incorporation into solid dosage forms, particularly into compressed tablets. Accordingly, the present invention provides granular powders, comprising a hydrophobic silicone oil, which can be incorporated into compressed tablets without excessive stickiness, and yet which yield the silicone oil easily on subsequent dissolution to give improved efficacy against plaque, mucilaginous and bacterial deposits.

SUMMARY OF THE INVENTION

According to a first aspect of the invention, there is provided a spray-dried, granular powder comprising
(i) from about 50% to about 99% of a water-soluble carrier,
(ii) from about 1% to about 50% of a hydrophobic silicone oil dispersed within the carrier,
wherein the spray-dried powder has a volume average particle size in the range from about 20 μm to about 500 μm, the powder being prepared by spray-drying an aqueous dispersion an aqueous dispersion of the silicone oil and the water-soluble carrier, characterised in that the silicone oil is present in the dispersion in the form of discrete droplets having a volume average droplet size in the range from about 0.5 μm to about 20 μm and that the ratio of the average spray-dried particle size to the average droplet size is at least about 2.5:1.

According to a further aspect of the invention, there are provided denture cleansers comprising the powder.

According to yet a further aspect of the invention, there are provided processes for manufacturing the powder.

All percentages and ratios herein are by weight of the powder, unless otherwise indicated.

DETAILED DESCRIPTION OF THE INVENTION

The powders of the invention thus comprise a water-soluble carrier and a hydrophobic silicone oil dispersed within the carrier as droplets, while preferred powders additionally comprise a silicone surfactant and a perfume or flavour oil. Each of these will be discussed in turn.

A first essential ingredient of the powder is a water-soluble carrier. By "water-soluble carrier" herein is meant any material which is has a solid at 25° C., is capable of being processed into granular form, is capable of being made into a clear or translucent aqueous solution at 25° C. at a level of about 1% by weight of the solution, and is safe for use on human skin or mucosa. Suitable carriers include, but are not limited to, polyethylene glycols, starches, gum arabic, gum tragacanth, gum acacia, carrageenans, cellulose derivatives and mixtures thereof. Preferably, the carrier is capable of being spray-dried into a free-flowing powder. In especially preferred embodiments the water-soluble carrier is a food-grade carrier selected from starches, gum arabic, gum tragacanth, gum acacia and mixtures thereof. A particularly preferred carrier is a modified starch available under the tradename Capsul E from National Starch & Chemical of Manchester, UK. Optionally, the carrier can comprise a sugar alcohol or saccharide, such as sorbitol, mannitol or maltodextrin. Without being limited by theory, it is believed that the sugar alcohol or saccharide helps to form a film on the surface of the particle which improves the encapsulation of the oil by the powder particle. A preferred carrier consists of a mixture of starch and sorbitol, preferably from about 2.5:1 to about 4:1, more especially about 3:1 by weight of the carrier. A mixture of gum acacia and maltodextrin in the ratio of from about 1:2 to about 2:1 can also suitably be used.

The water-soluble carrier is generally present in a level of from about 50% to about 99%, preferably from about 60% to about 90%, more preferably from about 65% to about 90% by weight.

A second essential ingredient of the powder is a hydrophobic silicone oil. By "hydrophobic silicone oil" herein is meant a polymer with a silicon or siloxane backbone that is insoluble in or immiscible with water at 25° C. and is liquid at 25° C.; or mixtures therof. Suitable classes of silicone oils include, but are not limited to, dimethicones, dimethiconols, dimethicone copolyols and aminoalkylsilicones.

Suitable aminoalkylsilicones are selected from noncyclic, hydrophobic aminoalkylsilicones having a formula comprising two basic units:
1) $(R^1)_m(R)_n SiO_{(4-m-n)/2}$ wherein m+n is 1, 2 or 3; n is 1, 2 or 3; m is 0, 1, 2; and
2) $(R_1)_a(R^2)_b SiO_{(4-a-b)/2}$ wherein a+b is 1, 2, or 3, and a and b are integers,
wherein $R^1$ and $R^2$ are independently selected from H, alkyl and alkenyl of about 1 to about 10 carbons optionally substituted with fluoro or cyano groups, hydroxy, alkoxy, and acetoxy, for example, wherein $R^1$ and $R^2$ are independently selected from methyl, ethyl, phenyl, vinyl, trifluoropropyl and cyanopropyl, and R is $R^4$ $R^4$

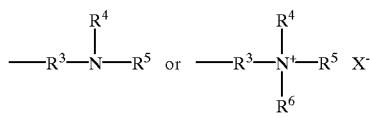

wherein $R^3$ is a divalent alkylene of about 1–20, preferably about 3–5 carbon atoms optionally substituted or interrupted by O atoms, $R^4$, $R^5$ and $R^6$ which may be the same or different are selected from H, alkyl of about 1–20, preferably about 1–10, more preferably about 1–4 carbons optionally substituted or interrupted by N and/or O atoms, and $X^-$ is a monovalent anion such as halide, hydroxide, and tosylate, said amino-alkylsilicone including from about 0.1–2%, preferably from about 0.5–2% of unit (1) on a repeating unit basis.

Preferred aminoalkylsilicones comprise amodimethicones. Amodimethicones are polydimethylsiloxane polymers containing aminoalkyl groups. The aminoalkyl groups may be present either pendant or at one or more ends of the polydimethylsiloxane chain. Preferred are aminoalkylsilicones in which aminoalkyl moiety R is selected from $(CH_2)_3NH_2$, $(CH_2)_3NHCH_2CH_2NH_2$, $(CH_2)_3N(CH_2CH_2OH)_2$, $(CH_2)_3NH_3^+X^-$, and $(CH_2)_3N(CH_3)_2(C_{18}H_{37})^+X^-$, and especially from $(CH_2)_3NH_2$ and $(CH_2)_3NH$—$CH_2CH_2NH_2$. Also preferred are aminoalkyl silicones having an average molecular weight of about 5,000 and above, preferably from about 5000 to about 100,000, more preferably from about 5000 to about 30,000.

Aminoalkyl silicone compounds suitable for use herein are well known. Methods of preparing aminoalkylsilicones are given in, for example, U.S. Pat. No. 2,930,809.

Examples of amodimethicones include OSI's Magnasoft fluid. These polymers comprise aminoalkyl groups affixed to a predominantly polydimethylsiloxane structure. The typical structure of Magnasofi's aminoalkyl group-containing units is —OSi(Me)$C_3H_6NHCH_2CH_2NH_2$.

Preferred for use herein are alkyl- and alkoxydimethicone copolyols and aminoalkylsilicones and mixtures thereof. Especially preferred are dimethicone copolyols selected from alkyl dimethicone copolyols and alkoxy dimethicone copolyols having the formula (I):

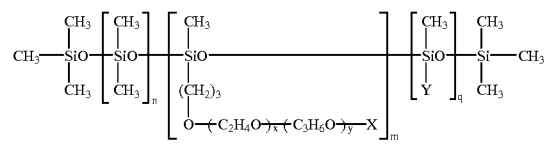

wherein X is selected from hydrogen, alkyl, alkoxy and acyl groups having from about 1 to about 16 carbon atoms, Y is selected from alkyl and alkoxy groups having from about 8 to about 22 carbon atoms, n is from 0 to about 200, m is from about 1 to about 40, q is from about 1 to about 100, the molecular weight of the residue $(C_2H_4O-)_x(C_3H_6O—)_yX$ is from about 50 to about 2000, preferably from about 250 to about 1000 and x and y are such that the weight ratio of oxyethylene:oxypropylene is from 100:0 to 0:100, preferably from 100:0 to about 20:80.

Such dimethicone copolyols have utility as antiplaque agents. In preferred embodiments, the dimethicone copolyol is selected from $C_{12}$ to $C_{20}$ alkyl dimethicone copolyols and mixtures thereof. Highly preferred is cetyl dimethicone copolyol marketed under the Trade Name Abil EM90.

The hydrophobic silicone oil is generally present in a level of from about 1% to about 35%, preferably from about 3% to about 35%, more preferably from about 5% to about 30% by weight.

The powders of the invention are in granular form, wherein the powder has a volume average particle size in the range from about 20 μm to about 500 μm, preferably from about 50 μm to about 250 μm, more preferably from about 80 μm to about 150 μm. The average particle size can be measured using standard sieve techniques well known in the art. Alternatively, the average particle size can be measured using a commercial instrument such as the Malvem Mastersizer X available from Malvern Instruments Ltd. of Malvem, Worcs., UK,. The Mastersizer is preferably fitted with a MSX64 Dry Powder Feeder and a a 300 mm lens for measuring particles in the range 1.2 to 600 microns.

The powders can be prepared by spray-drying an aqueous dispersion of the silicone oil and the water-soluble carrier. The dispersion can be prepared by mixing the silicone oil into an aqueous solution of the water-soluble carrier. Whilst, the strength of the carrier solution is not critical, it will be understood that very dilute solutions will require considerable input of energy to dry. Suitably the aqueous solution of the carrier will comprise from about 25% to about 50%, more preferably from about 30% to about 45%, more especially from about 35% to about 40% of the carrier by weight of the solution.

In order that the powder hereof has the desired properties, it is important to control the silicone oil droplet size within the dispersion. In general, the silicone oil should be present in the dispersion in the form of discrete droplets having a volume average droplet size in the range from about 0.5 μm to about 20 μm. Further, the ratio of the average spray-dried particle size to the average droplet size should be at least about 2.5:1. In preferred embodiments the ratio of the average spray-dried particle size to the average droplet size is at least about 4:1, preferably at least about 6:1, more preferably at least about 10:1. Smaller droplets, in relation to the final spray-dried powder particle size, serve to improve the flow characteristics and further processability of the powder.

The desired droplet size can be achieved by using shear mixing to form the dispersion and measured by using phase contrast photomicroscopy. A suitable procedure is to use, for example, a Nikon Labophot 2 at 400× magnification with fixed focal length and fitted with a graticule. It will be appreciated that a suitable number of observations need to be made to reduce the sampling error. The precise number to be made will depend, for example, upon the droplet size distribution achieved. The dispersion is mixed, with adjustment of the shear rate if necessary, until the desired droplet size is attained.

A desirable additional ingredient of the powders of the invention is a silicone surfactant having the general formula (I)

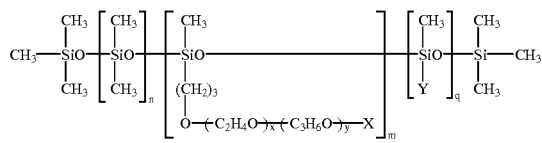

wherein X is selected from hydrogen, alkyl, alkoxy and acyl groups having from about 1 to about 16 carbon atoms, Y is $CH_3$, q is 0, n is from about 1 to about 100, m is from about 1 to about 40, the molecular weight of the residue $(C_2H_4O—)_x(C_3H_6O—)_y.X$ is from about 50 to about 2000, and x and y are such that the weight ratio of oxyethylene:oxypropylene is from about 100:0 to about 0:100.

The silicone surfactant, itself a dimethicone copolyol, assists in subsequent redispersion of the hydrophobic silicone in aqueous media whilst still allowing the hydrophobic silicone to deposit onto surfaces such as teeth, gums or artificial dentures. In preferred embodiments, the silicone surfactant is selected from dimethicone copolyols having a HLB value in the range from about 8 to about 14, more preferably from about 9 to about 12, and mixtures thereof. A suitable example of such a material is that marketed under the Trade Name Silwet L7230. The silicone surfactant is generally present in a level of from about 1% to about 25%, preferably from about 3% to about 15%, more preferably from about 5% to about 12% by weight of the powder. In general, the level of the silicone surfactant should be chosen such that the ratio of silicone surfactant to the hydrophobic silicone oil is from about 0.5:1 to about 5:1, more preferably from about 0.8:1 to about 3:1, most preferably from about 0.9:1 to about 2:1 by weight. Preferably the silicone surfactant is incorporated by making an intimate premix of the hydrophobic silicone oil and the silicone surfactant, and then forming a dispersion of the premix in the carrier solution as described above.

The powders of the invention preferably also include a flavour or perfume oil. As used herein, the term 'flavour or perfume oil' means those flavour or perfume essences and equivalent synthetic ingredients which are added to the powder for the principal purpose of modifying the taste and/or odour or other organoleptic sensations of the powder or the final product into which the powder is incorporated. It excludes hydrophobic silicone oils as described above but includes lipophilic physiological cooling agents.

Lipophilic flavorants suitable for use herein comprise one or more flavor components selected from wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof.

Physiological cooling agents suitable for use herein include carboxamides, menthane esters and menthane ethers, and mixtures thereof.

Suitable menthane ethers for use herein are selected from those with the formula:

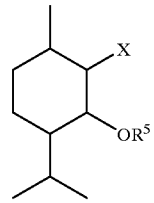

where $R_5$ is an optionally hydroxy substituted aliphatic radical containing up to 25 carbon atoms, preferably up to 5 carbon atoms, and where X is hydrogen or hydroxy, such as those commercially available under the trade name Takasago, from Takasago International Corporation. A particularly preferred cooling agent for use in the compositions of the present invention is Takasago 10 [3-1-menthoxy propan-1,2-diol (MPD)]. MPD is a monoglycerin derivative of 1-menthol and has excellent cooling activity.

The carboxamides found most useful are those described in U.S. Pat. No. 4,136,163, Jan. 23, 1979 to Wason et al., and U.S. Pat. No. 4,230,688, Oct. 28, 1980 to Rawsell et al. The amount of flavour or perfume oil employed is normally a matter of preference subject to such factors as flavour type, base type and strength desired. The level of flavour or perfume oil in the compositions of the invention is generally in the range from about 1% to about 15% by weight of the powder. Preferably the flavour or perfume oil is incorporated by making an intimate premix of the hydrophobic silicone oil and the flavour or perfume oil, along with the silicone surfactant, where used, and then forming a dispersion of the premix in the carrier solution as described above.

It has been found that forming an intimate admixture of the flavour or perfume oil with the hydrophobic silicone oil prior to dispersing the mixture in the aqueous carrier solution acts to reduce the droplet size of the dispersed oil and improve the flow characteristics and further processability of the powder.

It has further been found that the flavour or perfume oil being in intimate admixture with the hydrophobic silicone oil acts to enhance the substantivity of the flavour or perfume oil to teeth and/or dentures, thereby providing enhanced and/or sustained organoleptic impact. In the same way, lipophilic antimicrobial compounds can advantageously be included along in the same manner as the flavour or perfume oil, to provide enhanced and/or sustained anti-microbial efficacy. Suitable lipophilic anti-microbial compounds for use herein include thymol, menthol, triclosan, 4-hexylresorcinol, phenol, eucalyptol, benzoic acid, benzoyl peroxide, butyl paraben, methyl paraben, propyl paraben, salicylamides, and mixtures thereof.

The powders of the invention have a wide range of application. They may, for example be used to deliver antifoam activity to detergent compositions or to deliver skin conditioning benefits in face powders and the like. Preferably, however, the powders of the invention are incorporated into dental preparations in solid form, such as denture cleanser tablets compositions, toothpowders and the like, in order to deliver enhanced antiplaque activity. In preferred embodiments, the powders of the invention are incorporated into denture cleanser tablets compressed at a pressure of at least about $5 \times 10^4$ kPa.

In general, denture cleanser tablet compositions of the invention will comprise the powders of the invention at levels from about 1% to about 20%, preferably from about 3% to about 15%, more preferably from about 5% to about 10% by weight of the tablet.

Denture cleanser tablet compositions of the invention can additionally include one or more bleaching agents, organic peroxyacid precursors, effervescence generators, chelating agents, etc.

The bleaching agent takes the form of an inorganic persalt and can be selected from any of the well-known bleaching agents known for use in denture cleansers such as the alkali metal and ammonium persulfates, perborates, percarbonates and perphosphates and the alkali metal and alkaline earth metal peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. Of these, however, the alkali metal persulfates, perborates and mixtures thereof are prefered for use herein, highly preferred being the alkali metal perborates. Indeed, it is a feature of the invention that the tablet compositions herein will provide excellent antimicrobial activity even in the absence of alkali metal persulfates.

The amount of bleaching agent in the total composition is generally from about 5% to about 70% preferably from about 10% to about 50%. In compositions comprising a mixture of alkali metal persulfates and perborates, the overall persulfate:perborate ratio is suitably from about 5:1 to about 1:5, more especially from about 2:1 to about 1:2.

The denture cleansing compositions can also incorporate an effervescence generator, ie a material which in the presence of water releases carbon dioxide or oxygen with effervescence. The effervescence generator can be selected from generators which are effective under acid, neutral or alkaline pH conditions, but preferably it consists of a combination of a generator which is effective or most effective under acid or neutral pH conditions and a generator which is effective or most effective under alkaline pH conditions. Effervescence generators which are effective under acid or neutral pH conditions include a combination of at least one alkali metal carbonate or bicarbonate, such as sodium bicarbonate, sodium carbonate, sodium sesquicarbonate, potassium carbonate, potassium bicarbonate, or mixtures thereof, in admixture with at least one non-toxic, physiologically-acceptable organic acid, such as tartaric, fumaric, citric, malic, maleic, gluconic, succinic, salicylic, adipic or sulphamic acid, sodium fumarate, sodium or potassium acid phosphates, betaine hydrochloride or mixtures thereof. Of these, malic acid is preferred. Effervescence generators which are effective under alkaline pH conditions include persalts such as alkali and alkaline earth metal peroxoborates as well as perborates, persulphates, percarbonates, perphosphates and mixtures thereof as previously described, for example, a mixture of an alkali metal perborate (anhydrous, mono- or tetrahydrate) with a monopersulphate such as Caroat$^R$ marketed by EI du Point de Nemours Co. and which is a 2:1:1 mixture of monopersulphate, potassium sulphate and potassium bisulphate and which has an active oxygen content of about 4.5%.

In preferred denture cleansing compositions in tablet form, the effervescence generator takes the form of a solid base material which in the presence of water releases carbon dioxide or oxygen with effervescence. Suitably, the solid base material incorporates a (bi)carbonate/acid effervescent couple optionally in combination with a perborate/persulphate oxygen effervescence generator. The combination of generators is valuable for achieving optimum dissolution characteristics and pH conditions for achieving optimum cleaning and antimicrobial activity. The (bi) carbonate components generally comprise from about 5% to about 65%, preferably from about 25% to 55% of the total composition; the acid components generally comprise from about 5% to about 50%, preferably from about 10% to about 30% of the total composition.

The denture cleansing compositions of the invention can be supplemented by other known components of such formulations. An especially preferred additional component is an organic peroxyacid precursor, which in general terms can be defined as a compound having a titre of at least 1.5 ml of 0.1N sodium thiosulfate in the following peracid formation test.

A test solution is prepared by dissolving the following materials in 1000 mls distilled water:

| | |
|---|---|
| sodium pyrophosphate ($Na_4P_2O_7.10H_2O$) | 2.5 g |
| sodium perborate ($NaBO_2.H_2O_2.3H_2O$) having 10.4% available oxygen | 0.615 g |
| sodium dodecylbenzene sulphonate | 0.5 g |

To this solution at 60° C. an amount of activator is added such that for each atom of available oxygen present one molecular equivalent of activator is introduced.

The mixture obtained by addition of the activator is vigorously stirred and maintained at 60° C. After 5 minutes from addition, a 100 ml portion of the solution is withdrawn and immediately pipetted onto a mixture of 250 g cracked ice and 15 ml glacial acetic acid. Potassium iodide (0.4 g) is then added and the liberated iodine is immediately titrated with 0.1 N sodium thiosulphate with starch as indicator until the first disappearance of the blue colour. The amount of sodium thiosulphate solution used in ml is the titre of the bleach activator.

The organic peracid precursors are typically compounds containing one or more acyl groups, which are susceptible to perhydrolysis. The preferred activators are those of the N-acyl or O-acyl compound type containing a acyl radical R—CO wherein R is a hydrocarbon or substituted hydrocarbon group having preferably from about 1 to about 20 carbon atoms. Examples of suitable peracid precursors include:

1) Acyl organoamides of the formula $RCONR_1R_2$, where RCO is carboxylic acyl radical, $R_1$ is an acyl radical and $R_2$ is an organic radical, as disclosed in U.S. Pat. No. 3,117,148. Examples of compounds falling under this group include:
   a) N,N-diacetylaniline and N-acetylphthalimide;
   b) N-acylhydantoins, such as N,N'-diacetyl-5,5-dimethylhydantoin;
   c) Polyacylated alkylene diamines, such as N,N,N'N'-tetraacetylethylenediamine (TAED) and the corresponding hexamethylenediamine (TAHD) derivatives, as disclosed in GB-A-907,356, GB-A-907,357 and GB-A-907,358;
   d) Acylated glycolurils, such as tetraacetylglycoluril, as disclosed in GB-A-1,246,338, GB-A-1,246,339 and GB-A-1,247,429.
2) Acylated sulphonamides, such as N-methyl-N-benzoyl-menthane sulphonamide and N-phenyl-N-acetyl menthane sulphonamide, as disclosed in GB-A-3,183,266.
3) Carboxylic esters as disclosed in GB-A-836,988, GB-A-963,135 and GB-A-1,147,871. Examples of compounds of this type include phenyl acetate, sodium acetoxy benzene sulphonate, trichloroethylacetate, sorbitol hexaacetate, fructose pentaacetate, p-nitrobenzaldehyde diacetate, isopropeneyl acetate, acetyl aceto hydroxamic acid, and acetyl salicylic acid. Other examples are esters of a phenol or substituted phenol with an alpha-chlorinated lower aliphatic carboxylic acid, such as chloroacetylphenol and chloroacetylsalicylic acid, as disclosed in U.S. Pat. No. 3,130,165.

4) Carboxylic esters having the general formal Ac L wherein Ac is the acyl moiety of an organic carboxylic acid comprising an optionally substituted, linear or branched $C_6$–$C_{20}$ alkyl or alkenyl moiety or a $C_6$–$C_{20}$ alkyl-substituted aryl moiety and L is a leaving group, the conjugate acid of which has a pKa in the range from 4 to 13, for example oxybenzenesulfonate or oxybenzoate. Preferred compounds of this type are those wherein:

a) Ac is $R_3$—CO and $R_3$ is a linear or branched alkyl group containing from 6 to 20, preferably 6 to 12, more preferably 7 to 9 carbon atoms and wherein the longest linear alkyl chain extending from and including the carbonyl carbon contains from 5 to 18, preferably 5 to 10 carbon atoms, $R_3$ optionally being substituted (preferably alpha to the carbonyl moiety) by Cl, Br, OCH3 or $OC_2H_5$. Examples of this class of material include sodium 3,5,5-trimethylhexanoyloxybenzene sulfonate, sodium 3,5,5-trimethylhexanoyloxybenzoate, sodium 2-ethylhexanoyl oxybenzenesulfonate, sodium nonanoyl oxybenzene sulfonate and sodium octanoyl oxybenezenesulfonate, the acyloxy group in each instance preferably being p-substituted;

b) Ac has the formula $R_3(AO)_mXA$ wherein $R_3$ is a linear or branched alkyl or alkylaryl group containing from 6 to 20, preferably from 6 to 15 carbon atoms in the alkyl moiety, $R_5$ being optionally substituted by Cl, Br, $OCH_3$, or $OC_2H_5$, AO is oxyethylene or oxypropylene, m is from 0 to 100, X is O, $NR_4$ or CO-$NR_4$, and A is CO, CO—CO, $R_6$—CO, CO—$R_6$—CO, or CO—$NR_4$—$R_6$—CO wherein $R_4$ is $C_1$–$C_4$ alkyl and $R_6$ is alkylene, alkenylene, arylene or alkarylene containing from 1 to 8 carbon atoms in the alkylene or alkenylene moiety. Bleach activator compounds of this type include carbonic acid derivatives of the formula $R_3(AO)_mOCOL$, succinic acid derivatives of the formula $R_3OCO(CH_2)_2COL$, glycollic acid derivatives of the formula $R_3OCH_2COL$, hydroxypropionic acid derivatives of the formula $R_3OCH_2CH_2COL$, oxalic acid derivatives of the formula $R_3OCOCOL$, maleic and fumaric acid derivatives of the formula $R_3OCOCH=CHCOL$, acyl aminocaproic acid derivatives of the formula $R_3CONR_1(CH_2)_6COL$, acyl glycine derivatives of the formula $R_3CONRC_1CH_2COL$, and amino-6-oxocaproic acid derivatives of the formula $R_3N(R_1)CO(CH_2)_4COL$. In the above, m is preferably from 0 to 10, and R3 is preferably $C_6$–$C_{12}$, more preferably $C_6$–$C_{10}$ alkyl when m is zero and $C_9$—$C_{15}$ when m is non-zero. The leaving group L is as defined above.

5) Acyl-cyanurates, such as triacetyl- or tribenzoylcyanurates, as disclosed in U.S. Pat. No. 3,332,882.

6) Optionally substituted anhydrides of benzoic or phthalic acid, for example, benzoic anhydride, m-chlorobenzoic anhydride and phthalic anhydride.

Of all the above, preferred are organic peracid precursors of types 1(c) and 4(a).

Where present, the level of peroxyacid bleach precursor by weight of the total composition is preferably from about 0.1% to about 10%, more preferably from about 0.5% to about 5% and is generally added in the form of a bleach precursor agglomerate.

The bleach precursor agglomerates preferred for use herein generally comprise a binder or agglomerating agent in a level of from about 5% to about 40%, more especially from about 10% to about 30% by weight thereof. Suitable agglomerating agents include polyvinylpyrrolidone, poly (oxyethylene) of molecular weight 20,000 to 500,000, polyethyleneglycols of molecular weight of from about 1000 to about 50,000, Carbowax having a molecular weight of from 4000 to 20,000, nonionic surfactants, fatty acids, sodium carboxymethyl cellulose, gelatin, fatty alcohols, phosphates and polyphosphates, clays, aluminosilicates and polymeric polycarboxylates. Of the above, polyethyleneglycols are highly preferred, especially those having molecular weight of from about 1,000 to about 30,000, preferably 2000 to about 10,000.

Preferred from the viewpoint of optimum dissolution and pH characteristics are bleach precursor agglomerates which comprise from about 10% to about 75%, preferably from about 20% to about 60% by weight thereof of peroxyacid bleach precursor, from about 5% to about 60% preferably from about 5% to about 50%, more preferably from about 10% to about 40% of a (bi) carbonate/acid effervescent couple, from about 0% to about 20% of a peroxoboroate, and from about 5% to about 40%, preferably from about 10% to about 30% of an agglomerating agent. The final bleach precursor granules desirably have an average particle size of from about 500 to about 1500, preferably from about 500 to about 1,000 $\mu$m, this being valuable from the viewpoint of optimum dissolution performance and aesthetics. The level of bleach precursor agglomerates, moreover, is preferably from about 1% to about 20%, more preferably from about 5% to about 15% by weight of composition.

The denture cleansing compositions of the invention can be in tablet, granular or powder form, although tablet-form compositions are highly preferred herein. Compositions in tablet form can be single or multiple layered tablets.

Denture cleansing compositions of the invention can be supplemented by other usual components of such formulations, especially surfactants, chelating agents, enzymes, flavorants, physiological cooling agents, antimicrobial compounds, dyestuffs, sweeteners, tablet binders and fillers, foam depressants such as dimethylpolysiloxanes, foam stabilizers such as the fatty acid sugar esters, preservatives, lubricants such as talc, magnesium stearate, finely divided amorphous pyrogenic silicas, etc. The free moisture content of the final composition is desirably less than about 1% and especially less than about 0.5%.

Tablet binders and fillers suitable for use herein include polyvinyl-pyrrolidone, poly (oxyethylene) of molecular weight 20,000 to 500,000, polyethyleneglycols of molecular weight of from about 1000 to about 50,000, Carbowax having a molecular weight of from 4000 to 20,000, nonionic surfactants, fatty acids, sodium carboxymethyl cellulose, gelatin, fatty alcohols, clays, polymeric polycarboxylates, sodium carbonate, calcium carbonate, calcium hydroxide, magnesium oxide, magnesium hydroxide carbonate, sodium sulfate, proteins, cellulose ethers, cellulose esters, polyvinyl alcohol, alginic acid esters, vegetable fatty materials of a pseudocolloidal character. Of the above, polyethyleneglycols are highly preferred, especially those having molecular weight of from about 1,000 to about 30,000, preferably from about 12,000 to about 30,000.

The surface active agent used in the denture cleansing compositions of the invention can be selected from the many available that are compatible with the other ingredients of the denture cleanser, both in the dry state and in solution.

Such materials are believed to improve the effectiveness of the other ingredients of the composition by aiding their penetration into the interdental surfaces. Also, these materials aid in the removal of food debris attached to the teeth. Between 0.1 and 5 percent by weight of the dry composition of a dry powder or granular anionic surface active agent, such as sodium lauryl sulfate, sodium N-lauroylsarcosinate, sodium lauryl sulfoacetate or dioctyl sodium sulfosuccinate or ricinoleyl sodium sulfosuccinate, can, for example, be included in the composition and preferably the surface active agent comprises between 0.5 and 4 percent of the composition.

Suitable cationic, non-ionic and ampholytic surface active agents include, for example, quaternary ammonium compounds such as cetyltrimethyl-ammonium bromide, condensation products of alkylene oxides such as ethylene or propylene oxide with fatty alcohols, phenols, fatty amines or fatty acid alkanolamides, the fatty acid alkanolamides themselves, esters of long-chained ($C_8$–$C_{22}$) fatty acids with polyalcohols or sugars, for example glycerylmonostearate or saccharose monolaurate or sorbitolpolyoxyethylene-mono- or di-stearate, betaines, sulphobetaines or long-chain alkylaminocarboxylic acids.

Chelating agents beneficially aid cleaning and bleach stability by keeping metal ions, such as calcium, magnesium, and heavy metal cations in solution. Examples of suitable chelating agents include sodium tripolyphosphate, sodium acid pyrophosphate, tetrasodium pyrophosphate, aminopoly-carboxylates such as nitrilotriacetic acid and ethylenediamine tetracetic acid and salts thereof, and polyphosphonates and aminopolyphosphonates such as hydroxyethanediphosphonic acid, ethylenediamine tetramethylene-phosphonic acid, diethylenetriaminepentamethylenephosphonic acid and salts thereof. The chelating agent selected is not critical except that it must be compatible with the other ingredients of the denture cleanser when in the dry state and in aqueous solution. Advantageously, the chelating agent comprises between 0.1 and 60 percent by weight of the composition and preferably between 0.5 and 30 percent. Phosphonic acid chelating agents, however, preferably comprise from about 0.1 to about 1 percent, preferably from about 0.1% to about 0.5% by weight of composition.

Enzymes suitable for use herein are exemplified by proteases, alkalases, amylases, lipases, dextranases, mutanases, glucanases etc.

The following Examples further describe and demonstrate the preferred embodiments within the scope of the present invention.

EXAMPLES I TO III

The following are representative spray-dried powders according to the invention. The percentages are by weight of the spray-dried powder.

|  | I % | II % | III % |
|---|---|---|---|
| Abil EM 90[1] | 9.07 | 4.62 | 5.60 |
| Silwet L7230[2] | 11.37 | 5.79 | 11.10 |
| Peppermint flavour oil | 0.00 | 5.08 | 4.10 |
| Capsul E[3] | 59.67 | 63.38 | 58.07 |
| Sorbitol | 19.89 | 21.13 | 21.13 |
| Total | 100.00 | 100.00 | 100.00 |

[1]Cetyl dimethicone copolyol from Goldschmidt, a hydrophobic silicone.
[2]Dimethicone copolyol from Union Carbide, a silicone surfactant.
[3]Modified starch from National Starch & Chemical The powders are made according to the following process. An aqueous solution of the Capsul E and sorbitol is made by mixing 27.3 parts Capsul E, 9.1 parts sorbitol and 63.6 parts water, using conventional mixing techniques. A premix is made of the hydrophobic silicone, the silicone surfactant and (where used) the flavour, by blending using conventional mixing techniques to achieve intimate mixing. The premix is added to the mixing tank and the mixed at high shear, for example by using a Silverson L4RT mixer in the range from about 5000 to about 7000 rpm, to form a dispersion. A sample of the dispersion is taken for evaluation of the droplet size by phase contrast photomicroscopy. Mixer speed/configuration adjustments are made if necessary and the droplet size is re-evaluated. When the desired droplet size is achieved the dispersion is fed into a spray-dryer at from about 30 to about 100 psi with an inlet tempearture in the range from about 1 50° C. to about 220° C. and an outlet temperature in the range from about 80° C. to about 95° C. The powder is collected and stored in air-tight drums prior to use.

EXAMPLES IV TO VII

The following are representative denture cleanser tablets according to the invention. The percentages are by weight of the denture cleanser tablet.

The tablets are made by compressing a mixture of the granulated components in a punch and dye tabletting press at a pressure of about $2 \times 10^5$ kPa.

|  | IV | V | VI | VII |
|---|---|---|---|---|
| Malic Acid | 12.8 | — | 12 | — |
| Tartaric acid | — | 17.5 | 3.2 | 20.3 |
| Sodium Carbonate | 6.7 | 8 | 8 | 8.2 |
| Sulphamic Acid | 5 | 5 | 3 | 4 |
| PEG 10,000 | 5.9 | 3 | 5 | 5 |
| Sodium Bicarbonate | 21 | 23.2 | 23.9 | 22 |
| Sodium Perborate Monohydrate | 15 | 12 | 13 | 14 |
| Potassium Monopersulphate | 14.4 | 16 | 11 | 13.5 |
| Pyrogenic Silica | 0 | 0.3 | 0.1 | — |
| Talc | 2 | — | — | — |
| EDTA | — | — | 1 | 3 |
| EDTMP[1] | 1 | — | — | — |
| Flavor[4] | 2 | 1 | — | — |
| Bleach Precursor Agglomerate |  |  |  |  |
| TAED[2] | 2 | — | 4 | 2.5 |
| TMHOS[3] | 2 | 3 | — | — |
| Sulphamic Acid | 2 | 2 | 2 | 3.5 |
| Sodium Bicarbonate | 0.5 | 0.2 | 0.2 | 2 |
| PEG 6000 | 2.5 | 2 | 2.4 | 1.5 |
| Dye | — | 0.8 | 1.4 | 0.5 |
| Powder of Example I | 5.2 |  |  |  |
| Powder of Example II |  | 6.0 | 9.8 | — |
| Powder of Example III |  |  |  | 12.0 |
| Total | 100 | 100 | 100 | 100 |

[1]Ethylenediaminetetramethylenephosphonic acid
[2]Tetraacetylethylene diamine
[3]Sodium 3,5,5-trimethylhexanoyloxybenzene sulfonate
[4]Peppermint-based flavor In Examples IV to VII above, the overall tablet weight is 3 g; diameter 25 mm.

The denture cleansing tablets of Examples IV to VII display improved antiplaque, cleansing and anti-bacterial activity together with excellent cohesion and other physical and in-use performance characteristics.

What is claimed is:

1. A spray-dried, granular powder comprising:
   (i) from about 50% to about 99% of a water-soluble carrier;
   (ii) from about 3% to about 35% of a hydrophobic silicone oil dispersed within the carrier;

wherein the spray-dried powder has a volume average particle size in the range from about 20 $\mu$m to about 500 $\mu$m, the powder being prepared from an aqueous dispersion of the silicone oil and the water-soluble carrier, the silicone oil is present in the dispersion in the form of discrete droplets having a volume average droplet size in the range from about 0.5 $\mu$m, to about 20 $\mu$m and that the ratio of the average spray-dried particle size to the average droplet size is at least about 2.5:1.

2. A granular powder according to claim 1 wherein the hydrophobic silicone oil is selected from alkyl and alkoxy-dimethicone copolyols and aminoalkylsilicones and mixtures thereof.

3. A granular powder according to claim 2 wherein the hydrophobic silicone oil is a dimethicone copolyol selected from alkyl-dimethicone copolyols and alkoxydimethicone copolyols having the formula (I):

(I)

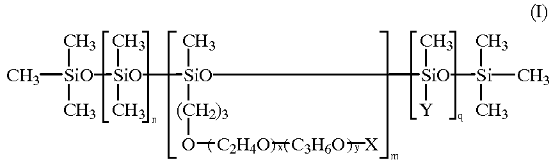

wherein X is selected from hydrogen, alkyl, alkoxy and acyl groups having from 1 to about 16 carbon atoms, Y is selected from alkyl and alkoxy groups having from about 8 to about 22 carbon atoms, n is from 0 to about 200, m is from about 1 to about 40, q is from about 1 to about 100, the molecular weight of the residue $(C_2H_4O—)_x(C_3H_6O—)_yX$ is from about 50 to about 2000, and x and y are such that the weight ratio of oxyethylene:oxypropylene is from 100:0 to 0:100.

4. A granular powder according to claim 2 wherein the hydrophobic silicone oil is cetyl dimethicone copolyol.

5. A granular powder according to claim 1 further comprising from about 1% to about 25% of a silicone surfactant of the general formula (I)

(I)

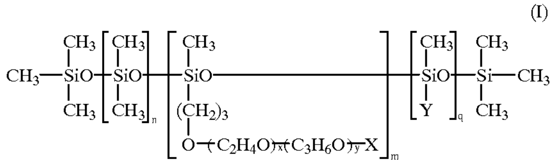

wherein X is selected from hydrogen, alkyl, alkoxy and acyl groups having from 1 to about 16 carbon atoms, Y is $CH_3$, q is 0, n is from about 1 to about 100, m is from about 1 to about 40, the molecular weight of the residue $(C_2H_4O—)_x—(C_3H_6O—)_yX$ is from about 50 to about 2000, and x and y are such that the weight ratio of oxyethylene:oxypropylene is from 100:0 to 0:100, the silicone surfactant being in intimate admixture with the hydrophobic silicone oil.

6. A granular powder according to claim 5 wherein the ratio of the silicone surfactant to the hydrophobic silicone oil is from about 0.5:1 to about 5:1 by weight.

7. A granular powder according to claim 6 wherein the ratio of the silicone surfactant to the hydrophobic silicone oil is from 0.8:1 to about 3:1 by weight.

8. A granular powder according to claim 7 wherein the ratio of the silicone surfactant to the hydrophobic silicone oil is from about 0.9:1 to about 2:1 by weight.

9. A granular powder according to claim 1 further comprising from about 1% to about 15% of a flavour or perfume oil, the flavour or perfume oil being in intimate admixture with the hydrophobic silicone oil.

10. A granular powder according to claim 1 wherein the ratio of the average spray-dried particle size to the average droplet size is at least about 4:1.

11. A granular powder according to claim 10 wherein the ratio of the average spray-dried particle size to the average droplet size is at least about 6:1.

12. A granular powder according to claim 11 wherein the ratio of the average spray-dried particle size to the average droplet size is at least about 10:1.

13. A granular powder according to claim 1 wherein the water-soluble carrier is a food-grade carrier selected from starches, gum arabic, gum tragacanth, gum acacia, and mixtures thereof.

14. A denture cleanser comprising:

(i) from about 1% to about 20% of the granular powder of claim 1, (ii)from about 5% to about 70% of a bleaching agent.

15. A denture cleanser according to claim 14 in compressed tablet form.

16. A process for manufacturing the granular powder of claim 5 comprising the steps of:

(i) making an intimate premix of the hydrophobic silicone oil and the silicone surfactant, (ii) mixing the premix with an aqueous solution of the water-soluble carrier under high shear until the droplets have a volume average particle size in the range from about 0.5 $\mu$m to about 20 $\mu$m, (iii) spray-drying the resulting mixture.

17. A process for manufacturing the granular powder of claim 9 comprising the steps of:

(i) making an intimate premix of the hydrophobic silicone oil, optionally the silicone surfactant and the perfume or flavour oil, (ii) mixing the premix with an aqueous solution of the water-soluble carrier under high shear until the droplets have a volume average particle size in the range from about 0.5 $\mu$m to about 20 Am, (iii) spray-drying the resulting mixture.

* * * * *